(12) United States Patent
Unkefer et al.

(10) Patent No.: US 9,290,443 B2
(45) Date of Patent: *Mar. 22, 2016

(54) PREPARATION OF 4-AMINO-2,4-DIOXOBUTANOIC ACID

(71) Applicants: Los Alamos National Security, LLC, Los Alamos, NM (US); New Mexico Highlands University, Las Vegas, NM (US)

(72) Inventors: Pat J. Unkefer, Los Alamos, NM (US); Rodolfo A. Martinez, Santa Fe, NM (US); David R. Glass, Las Vegas, NM (US)

(73) Assignees: Los Alamos National Security, LLC, Los Alamos, NM (US); New Mexico Highlands University, Las Vegas, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/489,329

(22) Filed: Sep. 17, 2014

(65) Prior Publication Data
US 2015/0065751 A1  Mar. 5, 2015

Related U.S. Application Data

(63) Continuation-in-part of application No. 13/828,905, filed on Mar. 14, 2013, now Pat. No. 9,045,392.

(60) Provisional application No. 62/040,376, filed on Aug. 21, 2014.

(51) Int. Cl.
*C07C 229/00* (2006.01)
*C07C 231/06* (2006.01)
*C07C 253/30* (2006.01)

(52) U.S. Cl.
CPC ........... *C07C 231/065* (2013.01); *C07C 253/30* (2013.01)

(58) Field of Classification Search
CPC   C07C 231/065; C07C 253/30; C07C 235/80; C07C 255/23; C08L 51/04; C08L 79/02; C08L 79/04; C08G 65/26; C08G 67/00; C08G 73/0233; C08G 73/06; C08K 5/357; C09D 179/04; C09J 179/04

See application file for complete search history.

(56) References Cited

U.S. PATENT DOCUMENTS

| 3,899,585 A | 8/1975 | Misato et al. |
| 4,336,397 A | 6/1982 | Cragoe, Jr. et al. |
| 5,922,649 A | 7/1999 | Pehu et al. |
| 6,083,876 A | 7/2000 | Jokinen et al. |
| 6,288,240 B1 | 9/2001 | Martinez et al. |
| 6,329,571 B1 | 12/2001 | Hiei |
| 6,448,202 B1 | 9/2002 | Miyazawa et al. |
| 6,555,500 B1 | 4/2003 | Unkefer et al. |
| 6,593,275 B1 | 7/2003 | Unkefer et al. |
| 6,703,346 B2 | 3/2004 | Herold et al. |
| 6,767,865 B2 | 7/2004 | Den Tandt et al. |
| 6,803,345 B2 | 10/2004 | Herold et al. |
| 6,831,040 B1 | 12/2004 | Unkefer et al. |
| 6,906,004 B2 | 6/2005 | Parrish et al. |
| 7,001,869 B2 | 2/2006 | Johnson |
| 7,094,735 B2 | 8/2006 | Herold et al. |
| 7,776,790 B2 | 8/2010 | Herold et al. |
| 8,551,917 B2 | 10/2013 | Unkefer et al. |
| 8,759,256 B2 | 6/2014 | Parrish et al. |
| 8,802,595 B2 | 8/2014 | Unkefer et al. |
| 9,045,392 B2 * | 6/2015 | Unkefer ............... C07C 253/30 |
| 2003/0032149 A1 | 2/2003 | Lalonde |
| 2003/0144147 A1 | 7/2003 | Herold et al. |
| 2003/0148889 A1 | 8/2003 | Herold et al. |
| 2003/0153461 A1 | 8/2003 | Parrish et al. |
| 2003/0153462 A1 | 8/2003 | Herold et al. |
| 2004/0063582 A1 | 4/2004 | Johnson |
| 2004/0127364 A1 | 7/2004 | Herold et al. |
| 2004/0132621 A1 | 7/2004 | Frisch et al. |
| 2004/0209777 A1 | 10/2004 | Gemma et al. |

(Continued)

FOREIGN PATENT DOCUMENTS

| EP | 10955565 A1 | 5/2001 |
| EP | 1647181 | 4/2006 |

(Continued)

OTHER PUBLICATIONS

International Search Report from PCT/US14/21620 dated Jun. 10, 2014 (citing US 4336397, Verbic, T. et al. and Tomassini, J. et al.).
Verbic, T. et al., An LFER study of the protolytic equilibria of 4-aryl-2,4-dioxobutanoic acids in aqueous solutions. Journal of the Serbian Chemical Society, Jan. 2007, 72(12):1201-1216. (cited in the International Search Report from PCT/US14/21620 dated Jun. 10, 2014).
Tomassini, J. et al., Inhibition of cap (m7GpppXm)-dependent endonuclease of influenza virus by 4-substituted 2,4-dioxobutanoic acid compounds. Antimicrob Agents Chemother, Dec. 1994, 38(12):2827-37. (cited in the International Search Report from PCT/US14/21620 dated Jun. 10, 2014).
Meister, A., Preparation and Enzymatic Reactions of the Keto Analogues of Asparagine and Glutamine. J. Biol. Chem., 1953, 200:571-589.

(Continued)

*Primary Examiner* — Yevegeny Valenrod
*Assistant Examiner* — Blaine G Doletski
(74) *Attorney, Agent, or Firm* — Mark D. Miller; William K. Nelson (57) ABSTRACT

A process for synthesizing 4-amino-2,4-dioxobutanoate involves reacting a dialkyl oxalate with an alkoxide in ethanol to form a reaction mixture, and afterward adding an alkyl cyano acetate to the reaction mixture and allowing a reaction to proceed under conditions suitable to form a first reaction product of the formula diethyl 2-cyano-3-hydroxy-butenedioate, and then isolating the diethyl 2-cyano-3-hydroxy-butenedioate, and afterward reacting the diethyl-2-cyano-3-hydroxy-butenedioate with an aqueous hydroxide under conditions suitable to form 4-amino-2,4-dioxobutanoate. The 4-amino-2,4-dioxobutanoate may be acidified into 4-amino-2,4-dioxobutanoic acid.

17 Claims, 9 Drawing Sheets

(56) References Cited

U.S. PATENT DOCUMENTS

| | | | |
|---|---|---|---|
| 2005/0137091 | A1 | 6/2005 | Herold et al. |
| 2005/0170967 | A1 | 8/2005 | Parrish et al. |
| 2005/0232868 | A1 | 10/2005 | Rennie et al. |
| 2006/0090219 | A1 | 4/2006 | Kisaka |
| 2006/0205601 | A1 | 9/2006 | Herold et al. |
| 2007/0105719 | A1 | 5/2007 | Unkefer et al. |
| 2010/0184599 | A1 | 7/2010 | Parrish et al. |
| 2012/0090365 | A1 | 4/2012 | Ersek et al. |
| 2014/0038824 | A1 | 2/2014 | Unkefer et al. |
| 2014/0275624 | A1 | 9/2014 | Unkefer et al. |
| 2015/0065750 | A1* | 3/2015 | Unkefer ............ C07C 231/065 562/567 |

FOREIGN PATENT DOCUMENTS

| | | |
|---|---|---|
| JP | S4629767 | 8/1971 |
| JP | H1059808 | 3/1998 |
| JP | 2005512963 | 5/2005 |
| RU | 2277323 | 6/2006 |
| RU | 2333245 | 9/2008 |
| WO | 0154500 | 8/2001 |
| WO | 03026429 | 4/2003 |
| WO | 2003026422 | 4/2003 |
| WO | 2004054360 | 7/2004 |
| WO | 2007056409 | 5/2007 |

OTHER PUBLICATIONS

Weygand, F., et al., Synthese von 1.5-Diaza-cyclooctan-dion-(4.8)-dicarbosaure-(2.6). Chemische Berichte, 1954, 87(4): 482-488.

Stephani, R.A., Meister, A., Structure of the Dimeric alpha-Keto Acid Analogue of Asparagine. The Jounrnal of Biological Chemistry, Dec. 1971, 246(23):7115-7118.

Ta, T.C., Joy, K.W., and Ireland, R.J., Utilization of the Amide Groups of Asparagine and 2-Hydroxysuccinamic Acid by Young Pea Leaves. Plant Physiology, 1984, 75: 527-530.

Tadashi, A. et al., Herbicidal Composition Containing Pyroglutamic Acid or its Salt, English Abstract of Japanese Patent Publication JPH1059808, Mar. 3, 1998. Machine-generated English translation. English Machine Translation of Japanese Patent Application Publication JP10059808 published on Mar. 3, 1998, the English Machine Translation was accessed and downloaded as early as Apr. 1, 2014.

Brochure: Take Off, Verdesian Life Sciences, LLC, 12 Pages, Aug. 2013.

Nanjo, T. et al., "Biological functions of proline in morphogenesis and osmotolerance revealed in antisense transgenic Arapidopsis thanliana." The Plant Journal, vol. 18, No. 2 (Feb. 1999) pp. 185-193.

Walkey et al., "The inactivation of virus in cultured shoot tips of Nicotiana rustica L." J. Gen. Virol., 1969, 5, 237-241.

English Abstract of Japanese Patent Publication JP2005512963, published May 12, 2005. The English abstract was accessed and downloaded from European Patent Organization, http://www.epo.org/searching/free/espacenet.html on Aug. 20, 2014.

English Abstract of WIPO Patent Publication WO2007056409 published on May 18, 2007. The English abstract was accessed and downloaded from European Patent Organization, http://www.epo.org/searching/free/espacenet.html on Oct. 17, 2014.

English Abstract of Russian Patent Publication RU2277323 published on May 10, 2006. The English abstract was accessed and downloaded from http://bd.patent.su/2277000-2277999/pat/servl/servlet4b05.html on Oct. 17, 2014.

Method of Constructing Plant Showing Improved Growth Under Regulation of Nitrogen, English Abstract of Russian Patent Publication RU2333245, Sep. 10, 2008, European Patent Organization, http://www.epo.org/searching/free/espacenet.html.

English Abstract of Russian Patent Publication RU2006104849 published on Jun. 27, 2006. (Issued as RU2333245). The English abstract was accessed and downloaded from European Patent Organization, http://www.epo.org/searching/free/espacenet.html on Oct. 17, 2014.

Frisch, G. et al., Microemulsion Concentrates, English Abstract of WIPO Patent Publication WO2004054360, Jul. 1, 2004, European Patent Organization, http://www.epo.org/searching/free/espacenet.html.

International Search Report from WO03026429 dated May 12, 2002.

Rooney et al., "Inhibitors of Glycolic Acid Oxidase. 4-Substituted 3-Hydroxy-1H-pyrrole-2,5-dione derivatives," J. Med. Chem., 1983, vol. 26, pp. 700-714.

Williams et al., "Inhibitors of Glycolic Acid Oxidase. 4-Substituted 2,4-Dioxobutanoic Acid Derivatives," J. Med. Chem., 1983, vol. 26, pp. 1196-1200.

Weygand, F., et al., Synthese von 1.5-Diaza-cyclooctan-dion-(4.8)-dicarbosaure-(2.6). Chemische Berichte, 1954, 87(4): 482-488—with English Abstract.

International Patent Application No. PCT/US2014/050274, International Search Report dated Nov. 18, 2014.

International Patent Application No. PCT/US2014/050274, Written Opinion of the International Search Authority dated Nov. 18, 2014.

\* cited by examiner

X-ray Crystal structure of diethyl 2-cyano-3-hydroxy-butenedioate

PREPARATION OF 4-AMINO-2,4-DIOXOBUTANOIC ACID

PRIORITY

This application is a continuation-in-part of U.S. application Ser. No. 13/828,905 filed on Mar. 14, 2013, and this application also claims the benefit of U.S. provisional application Ser. No. 62/040,376 filed on Aug. 21, 2014, both of which are incorporated herein by this reference.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates to the preparation of 4-amino-2,4-dioxobutanoate, including 4-amino-2,4-dioxobutanoic acid.

BACKGROUND OF THE INVENTION

The compound 4-amino-2,4-dioxobutanoic acid is a metabolite found in plants (see, for example: Ta et al., "Utilization of the Amide Groups of Asparagine and 2-Hydroxysuccinamic Acid by Young Pea Leaves," Plant Physiology, July 1984, vol. 75, pp. 527-530, incorporated by reference). Meister reported in "Preparation and Enzymatic Reactions of the Keto Analogues of Asparagine and Glutamine," J. Biol. Chem., vol. 200, (1953), pp. 571-589, which is incorporated by references, a process for synthesizing 4-amino-2,4-dioxobutanoic acid. This preparation was on a small scale and was expensive because it required crude rattlesnake venom.

SUMMARY OF THE INVENTION

The present invention provides processes for synthesizing 4-amino-2,4-dioxobutanoate, including 4-amino-2,4-dioxobutanoic acid. One such process involves reacting diethyl oxalate (or any suitable dialkyl oxalate) with a suitable alkoxide (such as, without limitation, sodium, potassium, lithium, cesium, calcium) in a suitable solvent to form a reaction mixture, and afterward adding ethyl cyanoacetate (or any suitable alkyl cyanoacetate) to the reaction mixture and allowing a reaction to proceed under conditions suitable to form a first reaction product of the formula diethyl 2-cyano-3-hydroxy-butenedioate, and isolating said first reaction product of diethyl 2-cyano-3-hydroxy-butenedioate, and then reacting said first reaction product of diethyl 2-cyano-3-hydroxy-butenedioate with a suitable aqueous hydroxide (such as, without limitation, sodium, potassium, lithium, cesium, calcium) under conditions suitable to form 4-amino-2,4-dioxobutanoate (alkali salt). Once acidified (using an acid such as, without limitation, hydrochloric, phosphoric, formic, sulfuric), the resulting product is 4-amino-2,4-dioxobutanoic acid.

In an embodiment, a process for synthesizing 4-amino-2,4-dioxobutanoic acid includes the steps of reacting diethyl oxalate with an alkoxide (such as, without limitation, sodium, potassium, lithium, cesium, calcium) in an alcoholic solvent to form a reaction mixture, then adding ethyl cyanoacetate to the reaction mixture. It is to be appreciated that any suitable dialkyl oxalate may be substituted for the diethyl oxalate, and that any suitable alkyl cyanoacetate may be substituted for ethyl cyanoacetate in these steps. After allowing the ingredients to react, the reaction mixture was extracted using dichloromethane and water. The aqueous layer was separated from the dichloromethane layer, acidified, and extracted with additional dichloromethane. In some embodiments, the dichloromethane layers may then be combined; however in this case they were not. Removal of the dichloromethane left diethyl 2-cyano-3-hydroxy-butenedioate. The diethyl 2-cyano-3-hydroxy-butenedioate was combined with an aqueous hydroxide (such as, without limitation, sodium, potassium, lithium, cesium, calcium) to form a reaction mixture that was subjected to conditions suitable for forming 4-amino-2,4-dioxobutanoate (alkali salt). Once acidified (using an acid such as, without limitation, hydrochloric, phosphoric, formic, sulfuric), the resulting product is 4-amino-2,4-dioxobutanoic acid.

An alternative process for synthesizing 4-amino-2,4-dioxobutanoic acid involves reacting diethyl oxalate (or any suitable dialkyl oxalate) with a suitable alkoxide (such as, without limitation, sodium, potassium, lithium, cesium, calcium) in a suitable solvent to form a reaction mixture, and afterward adding acetonitrile to the reaction mixture and allowing a reaction to proceed under conditions suitable to form a first reaction product in the form of an alkali salt, such as, for example, ethyl 3-cyano-2-oxopropenolate sodium salt, isolating said first reaction product, and then reacting said first reaction product with either an ion exchange resin (such as, without limitation, Amberlyst A-26 resin), or with a suitable aqueous hydroxide (such as, without limitation, sodium, potassium, lithium, cesium, calcium) under conditions suitable to form 4-amino-2,4-dioxobutanoate (alkali salt). Once acidified (using an acid such as, without limitation, hydrochloric, phosphoric, formic, sulfuric), the resulting product is 4-amino-2,4-dioxobutanoic acid.

DETAILED DESCRIPTION

Figure 1:
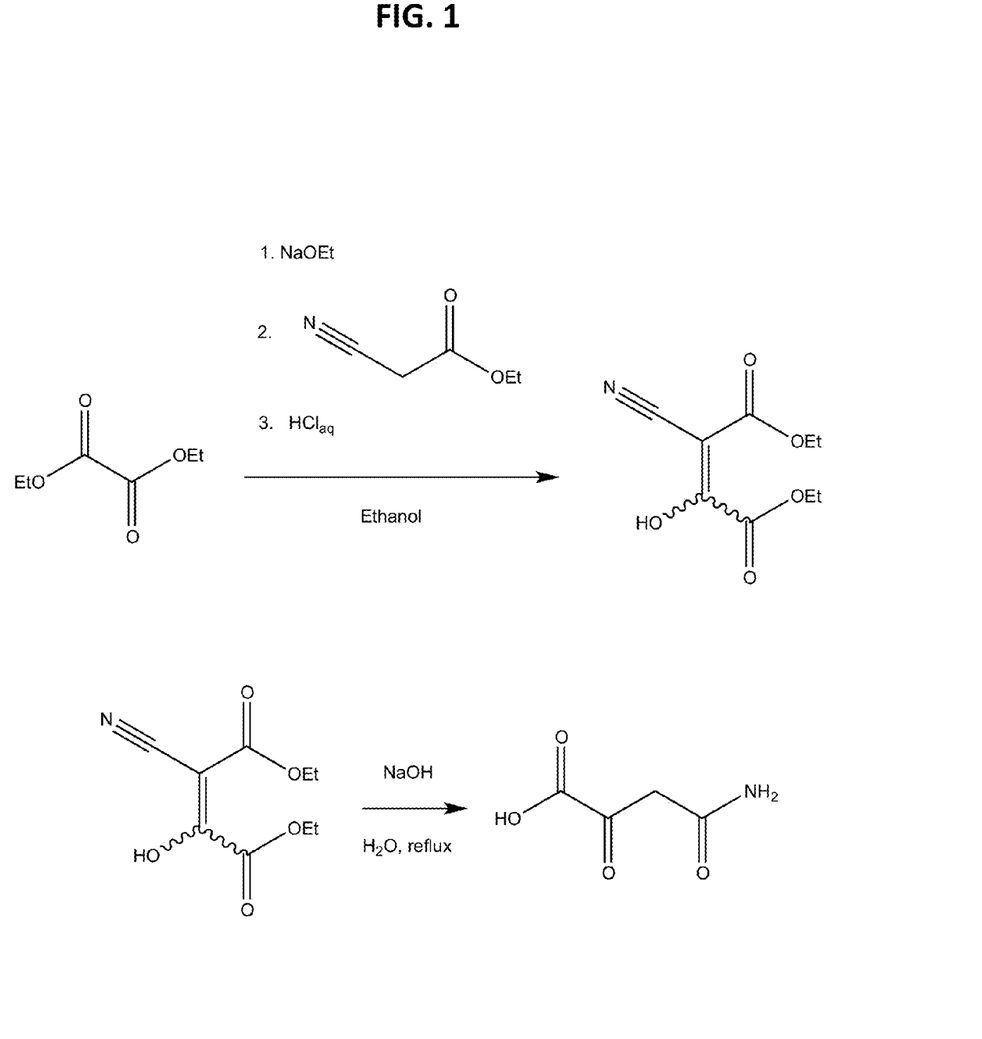
FIG. 1 is a typical reaction scheme for synthesis of 4-amino-2,4-dioxobutanoic acid.
Figure 2:
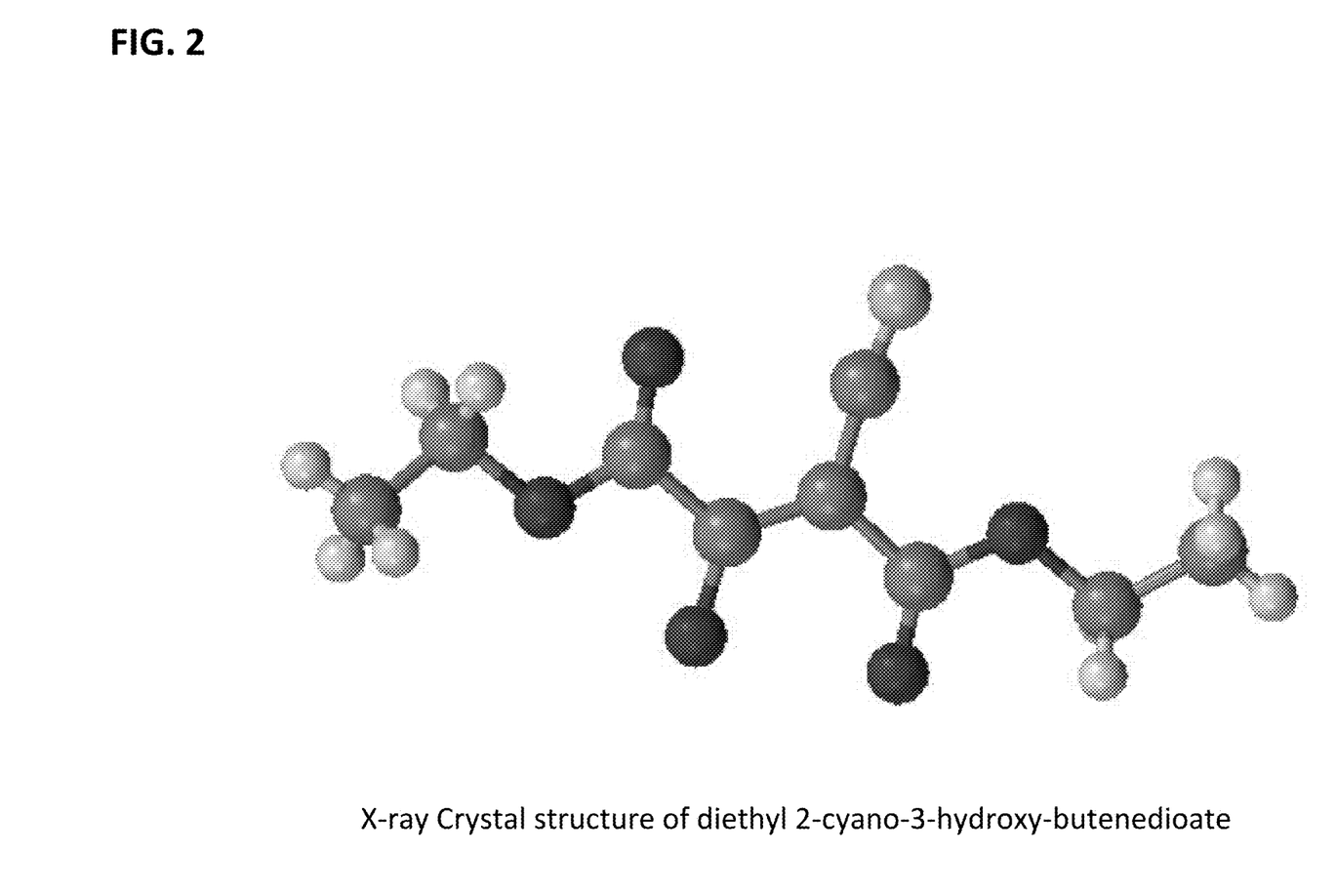
FIG. 2 is an x-ray crystal structure of diethyl 2-cyano-3-hydroxy-butenedioate.

This invention is concerned with the synthesis of 4-amino-2,4-dioxobutanoic acid and derivatives thereof. An exemplary reaction sequence begins by reacting sodium metal with ethanol to form sodium ethoxide, then adding diethyl oxalate to the sodium ethoxide, and then slowly adding ethyl cyanoacetate. It is to be appreciated that potassium, lithium, cesium, calcium or other metals may alternatively be used instead of sodium to form the ethoxide. An acidic workup resulted in diethyl 2-cyano-3-hydroxy-butenedioate which was isolated as a pale yellowish solid. Without further purification, the diethyl 2-cyano-3-hydroxy-butenedioate was heated in the presence of aqueous sodium hydroxide. It is to be appreciated that potassium, lithium, cesium, calcium or other metals may alternatively be used instead of sodium as the hydroxide. These chemical reactions are shown in FIG. 1.

The details of a typical diester synthesis now follow. An exemplary synthesis of diethyl 2-cyano-3-hydroxy-butenedioate began by fitting a dry 5-liter Morton flask with a reflux condenser. Absolute ethanol (1040 milliliters) was added to the flask under nitrogen, and sodium metal (35.2 g, 1.53 moles, 1.0 equivalent) was placed into the absolute ethanol also under nitrogen while an ice-water bath was used to cool the flask. After the mixture was stirred for about 6 hours, the ice water bath was removed and the reaction was brought to room temperature. The temperature rose briefly to about 30° C. After about 24 hours, the sodium metal had completely dissolved. Diethyl oxalate (219.2 grams, 1.5 moles, 1.0 equivalent) was added neat in a single portion to the flask. While the reaction mixture was stirring, a solution of ethyl cyanoacetate (169.7 grams, 1.5 moles, 1.0 equivalent) in absolute ethanol (1000 milliliters) was added dropwise at room temperature to the reaction mixture. The addition, which was made at a rate of 1 drop every 2 to 3 seconds, took about 2½ days to complete. Afterward, the reaction mixture was extracted with dichloromethane (1000 milliliters) and deionized water (1000 milliliters). The aqueous layer was extracted with an additional 100 milliliters dichloromethane. The resulting aqueous layer had a pH of about 8-9. The layers were separated. The aqueous layer was acidified to a pH of about 1 with 6 M HCl. The acidic aqueous layer was then extracted with dichloromethane (1000 milliliters) and the layers were separated. The organic layer was evaporated by rotary evaporator to yield diethyl 2-cyano-3-hydroxy-butenedioate as a pale yellowish solid (304 grams, 95%) that was used without any further purification.

The 4-amino-2,4-dioxobutanoate was synthesized using the diethyl-2-cyano-3-hydroxy-butenedioate prepared as described above. A 5-liter Morton flask was equipped with an air condenser. Diethyl 2-cyano3-hydroxy-butenedioate (214.2. grams, 1.00 mole, 1.0 equivalent) was dissolved in aqueous sodium hydroxide (1.0 M, 1000 milliliters, 4.0 equivalents) at room temperature in the flask while stirring the contents of the flask. After about one minute, a heating mantle was placed underneath the flask. Using the heating mantle, the flask was heated sufficiently for reflux while the reaction mixture was stirred. After about 4½ hours at reflux, the heat was removed and the reaction mixture was allowed to cool to room temperature and was stirred overnight at room temperature. The reaction solution was placed into an ice-water bath and acidified using 6M HCl until the pH of was equal to about 1. Solids formed after about 5 minutes. The solids were filtered. The colorless solids (27 grams) were analyzed by NMR and were found to include carbonate (13C-NMR δ=162 ppm). The bulk of the water was evaporated using a rotary evaporator at about 40° C. The solids were stirred in acetone (1000 milliliters) and then filtered. The acetone was then removed under a vacuum using a rotary evaporator followed by a vacuum pump to yield 4-amino-2, 4-dioxobutanoate (alkali salt). Once acidified (using an acid such as, without limitation, hydrochloric, phosphoric, formic, sulfuric), the resulting product was the 4-amino-2,4-dioxobutanoic acid in 56% yield (74 grams) as a light yellow solid that was used without further purification.

Figure 4:
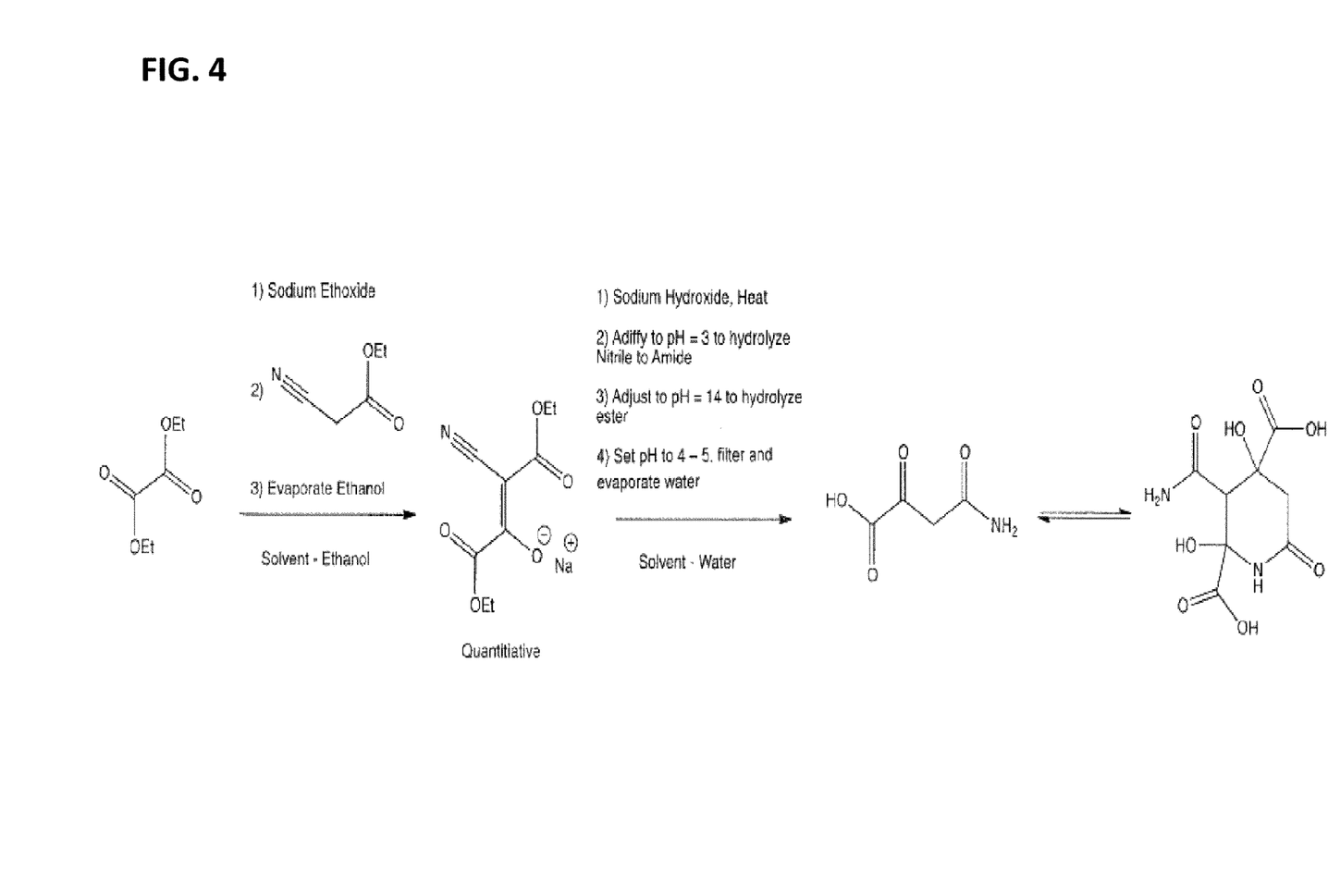
FIG. 4 is a diagram of an embodiment of an overall process of the present invention.

The details of another exemplary synthesis now follow. (See FIG. 4.) In a dry 3-L round bottom flask fitted with a reflux condenser, sodium metal (21.5 g, 0.935 mol, 1.0 eq) was placed into absolute ethanol (690 mL) under argon, in a room temperature water bath for 24 hours while stirring. The temperature did not rise from ambient. After 24 hours, the sodium metal had completely reacted to form sodium ethoxide. A dialkyl oxalate, in this case diethyl oxalate (136.5 g, 0.935 mol, 1.0 eq) was added neat in a single portion, and then and alkyl cyanoacetate, in this case ethyl cyanoacetate (105.7 g, 0.935 mol, 1.0 eq) as a solution in absolute ethanol (500 mL) was added dropwise at room temperature while stirring. This addition was made at a rate of 1 drop every 2-3 seconds, and took about 1½ days to complete. The volatiles were evaporated by rotary evaporator to yield an alkali salt, in this case diethyl 2-cyano-3-hydroxy-butenedioate sodium salt as a pale yellowish sticky solid and residual ethanol. This material was used without further purification in the subsequent step (239 g, quantitative, 92.3% pure by mass).

In a 1-L round bottom flask, the alkali salt diethyl 2-cyano-3-hydroxy-butenedioate sodium salt (11.2 g, 0.0475 mol, 1.0 eq) was dissolved in aqueous sodium hydroxide (1M, 95 mL, 0.095 mol, 2.0 eq) at room temperature. After one minute, the diethyl 2-cyano-3-hydroxy-butenedioate sodium salt was completely dissolved and the flask was placed into a preheated heating mantle. The solution was heated at reflux with stirring for 4½ hours. The homogeneous solution was then removed from heat and stirred at room temperature overnight. The homogeneous solution was then placed into an ice-water bath and acidified to pH=3 using 6M HCl (10 mL) It is important to note here that pH 4 will not hydrolyze the cyano group, and pH lower than 3 risks hydrolyzing the amide. The reaction bubbled, which indicated the liberation of $CO_2$. An aliquot was examined by $^{13}$C-NMR, and showed that the cyano group had been hydrolyzed to the amide and that the reaction had decarboxylated. This was ascertained by the disappearance of the signal at ~120 ppm and appearance of a new peak at ~172. The reaction was then treated with 6M sodium hydroxide (13 mL) to adjust the pH to 14. The reaction was stirred at room temperature for approximately 5 days. As the reaction stirred, it became heterogeneous. At this time the solution was yellow. An aliquot was evaporated to show that the ester (NMR peaks at 62 and 13 ppm) had been 90% hydrolyzed. The reaction was then filtered to remove 3.8 grams colorless solid that did not comprise the desired product. After this filtration was performed, the homogeneous solution was placed into a room-temperature water bath. The reaction was then acidified to pH=4.5 using 1M HCl (20 mL). The reaction volume was reduced by 75 mL using a rotary evaporator (from its initial volume of 105 mL). At this time, solids began to precipitate and the reaction was left to sit overnight at room temperature (pH=4-5). The reaction was filtered, removing 1.4 grams colorless solid that did not comprise the desired product. The volume was reduced by half on the rotary evaporator, and 2-propanol (2 mL) was added. Solids formed immediately. The solids were removed by filtration to yield 1.4 grams of colorless solid that did not comprise the desired product. The remaining solution was evaporated by rotary evaporator followed by high-vacuum pump to yield a yellow solid (5.0 g, 81%). $^{13}$C-NMR ($D_2O$, 75 MHz): δ=176.1, 175.2, 174.2, 44.9.

Figure 3:
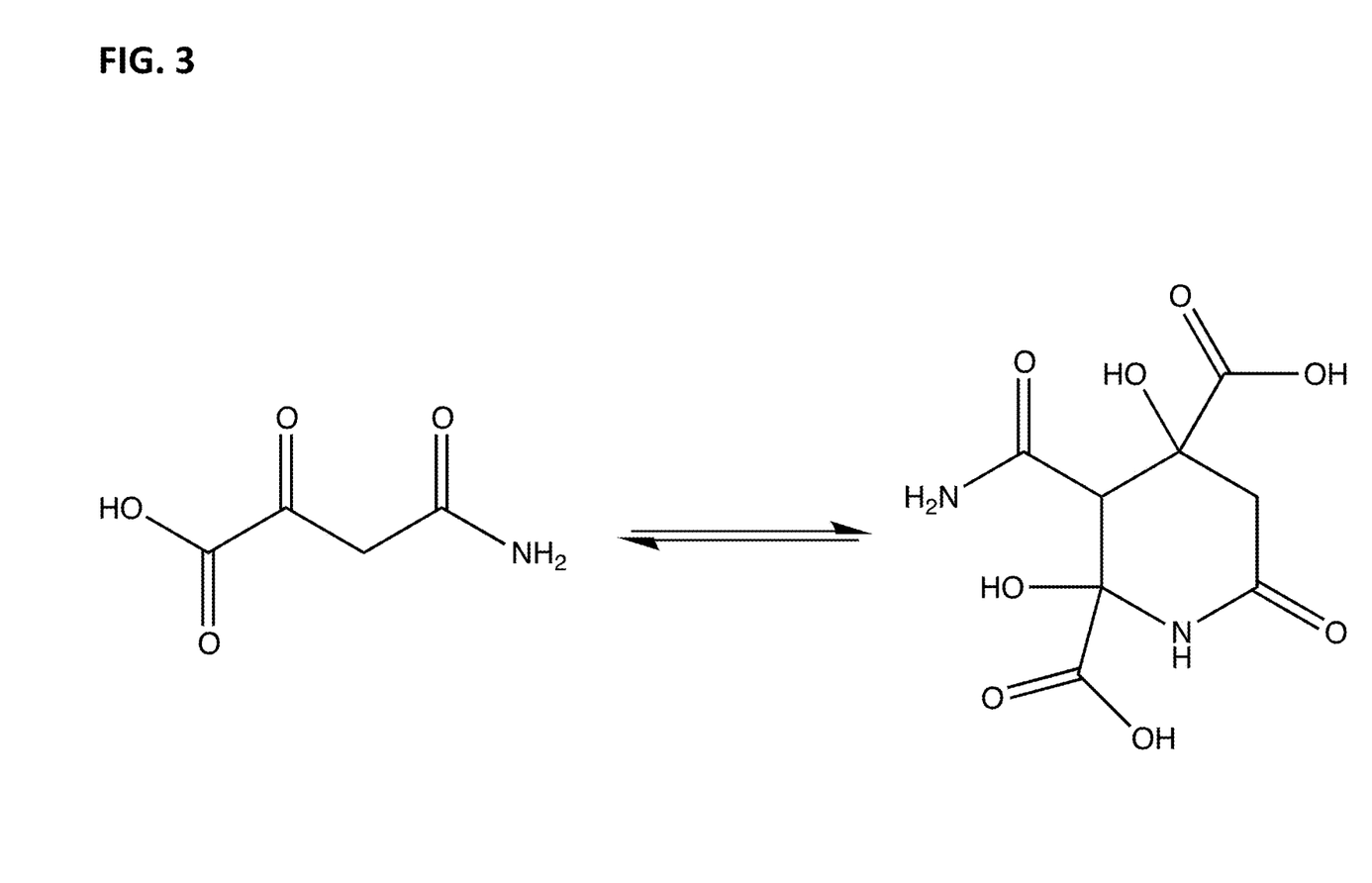
FIG. 3 shows different forms of 4-amino-2,4-dioxobutanoic acid that may be made by the synthesis of the present invention.

NMR indicates that the monomer and dimeric forms of the compound are in equilibrium as shown in FIG. 3.

An alternative synthesis of 4-amino-2,4-dioxobutanoate using acetonitrile and diethyl oxalate is set forth in FIG. 5 and in the following discussion.

In this exemplary synthesis, a dry 2-L round bottom flask fitted with a reflux condenser, sodium metal (10.7 g, 0.465 mol, 1.0 eq) was placed into absolute ethanol (700 mL) under argon, in a room temperature water bath for 24 hours while stirring. The temperature did not rise from ambient. After 24 hours, the sodium metal had completely reacted to form sodium ethoxide. A dialkyl oxalate, in this case diethyl oxalate (68.0 g, 0.465 mol, 1.0 eq) was added neat in a single portion, and then acetonitrile (19.1 g, 0.465 mol, 1.0 eq) was added neat in a single portion. The reaction was refluxed for 12 hours. The reaction was cooled in an ice-water bath and then filtered. The solids were rinsed with absolute ethanol, and then dried by vacuum to yield an alkali salt, in this case ethyl 3-cyano-2-oxopropenolate sodium salt, as a tan solid (48.2 g, 63%). This material was used without further purification in the subsequent step. In a 100-mL round bottom flask, the ethyl 3-cyano-2-oxopropenolate sodium salt (3.5 g, 0.022 mol, 1.0 eq) was dissolved in aqueous sodium hydroxide (1M, 22 mL, 0.022 mol, 1.0 eq) at room temperature.

Hydrogen peroxide (30%, 7.5 g, 0.066 mol, 3.0 eq) was added to the ice bath-cooled solution. A ion exchange resin, in this case Amberlyst A-26 resin (22 grams, 1 g/mmol eq) was added to the stirring solution. The solution was permitted to come to room temperature as the cooling bath warmed. The solution was stirred for 18 hours at room temperature, and $^{13}$C-NMR shows conversion of the nitrile to the amide.

It is important to recognize that hydrolysis of the nitrile to the amide using acid and base conditions is another way to complete the synthesis. While hydrolysis will ultimately produce the desired compound, it may be problematic to control, and the yields may vary. The alternative method of using hydrogen peroxide and Amberlyst A-26 (—OH form) is more reliable and is therefore preferred.

Figure 6:
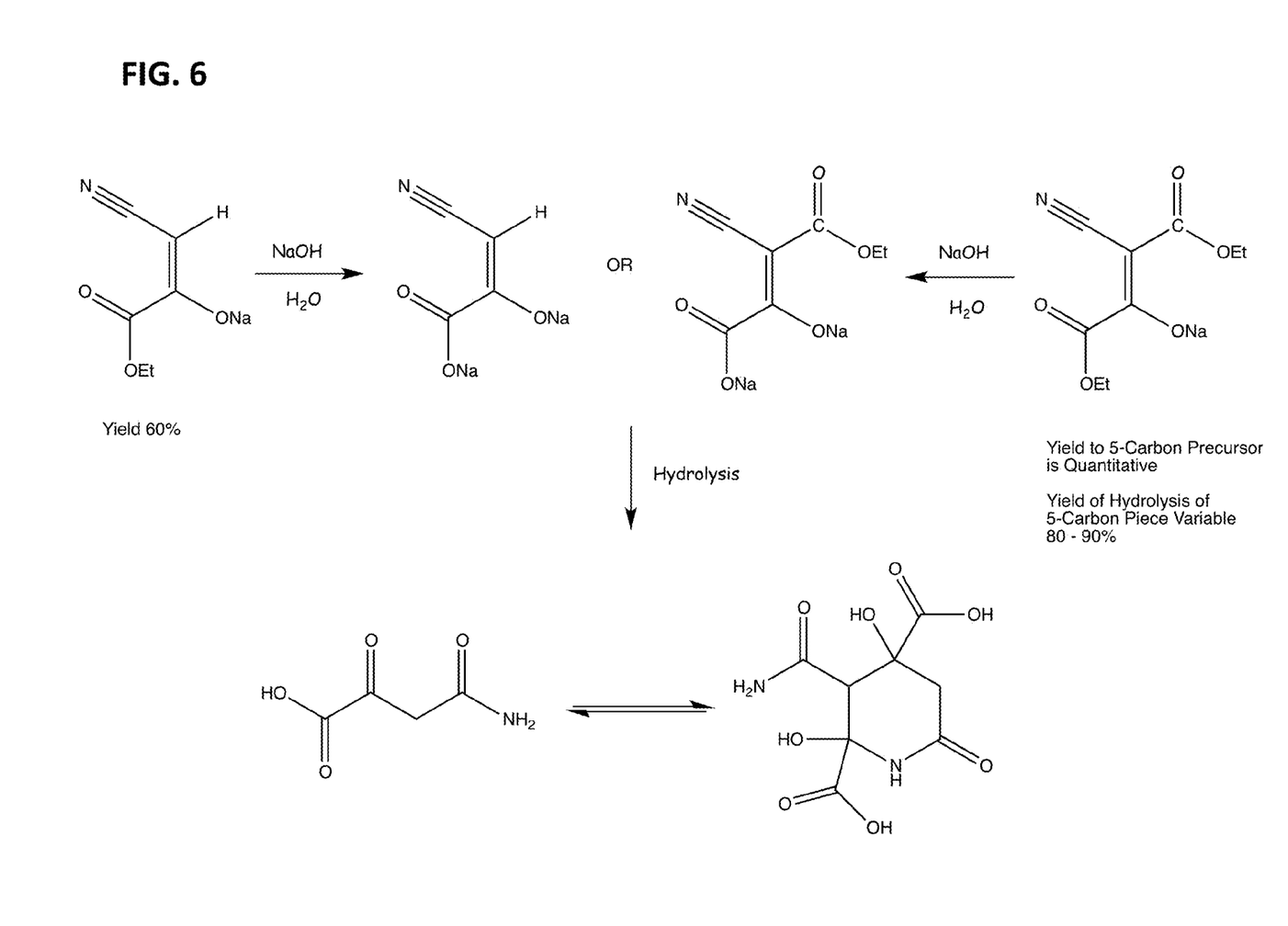
FIG. 6 is a comparison of alternative pathways of the present invention for forming 4-amino-2,4-dioxobutanoic acid.

The scheme in FIG. 6 shows how the 4-amino-2,4-dioxobutanoic acid or salt compound may be produced by either pathway.

Figure 7:
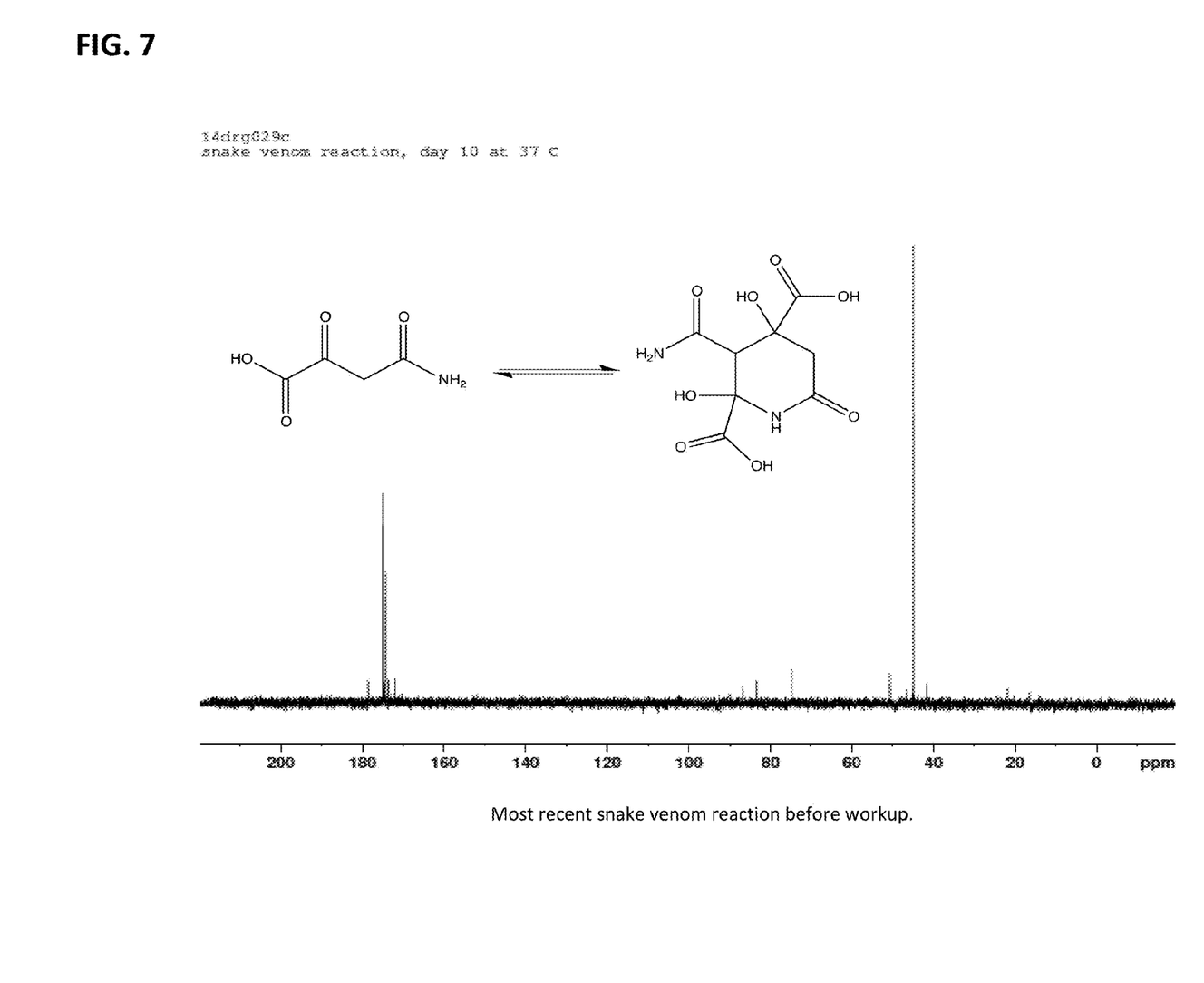
FIG. 7 is a spectrum taken before workup.
Figure 8:
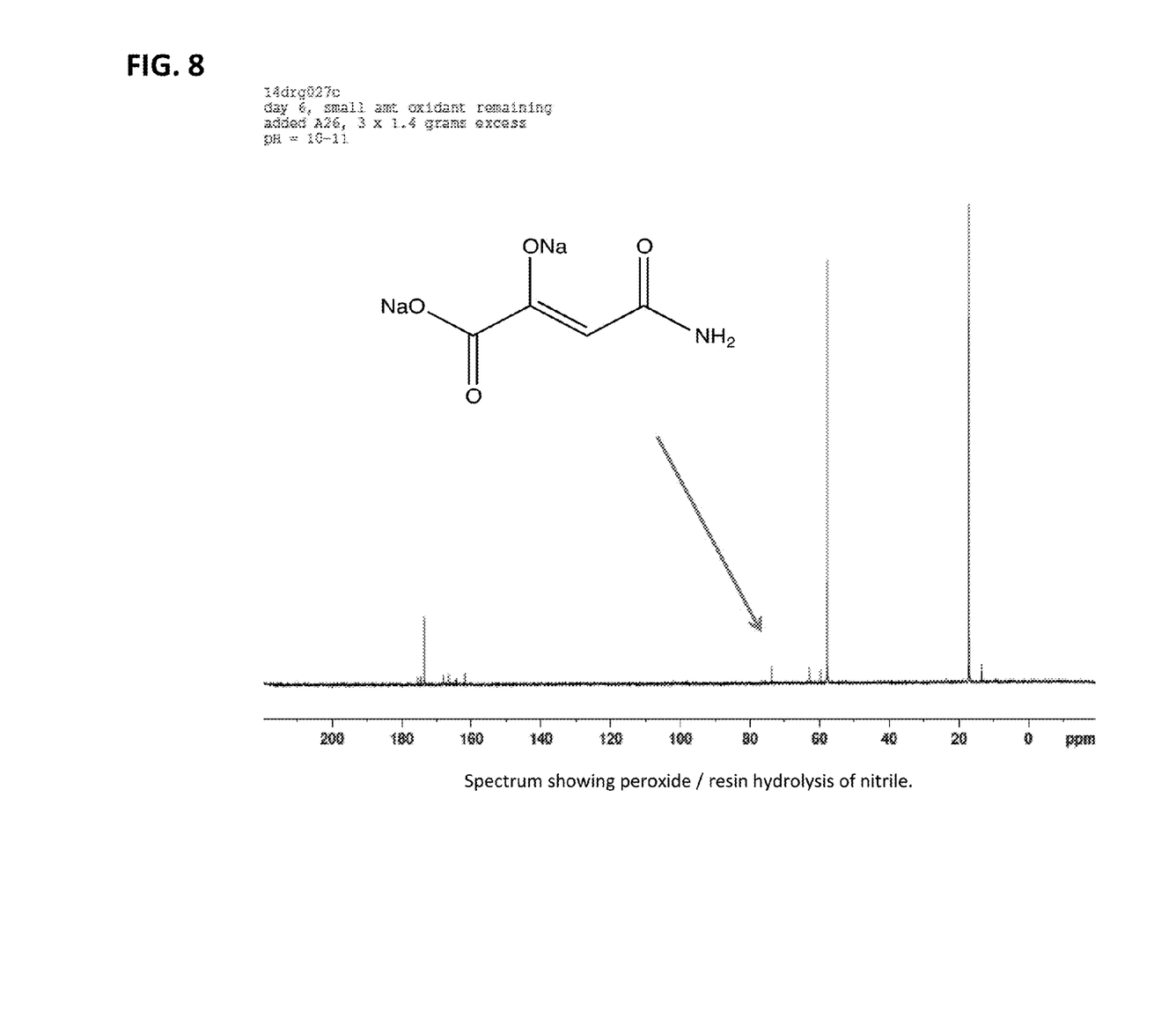
FIG. 8 is a spectrum showing peroxide/resin hydrolysis of nitrile.
Figure 9:
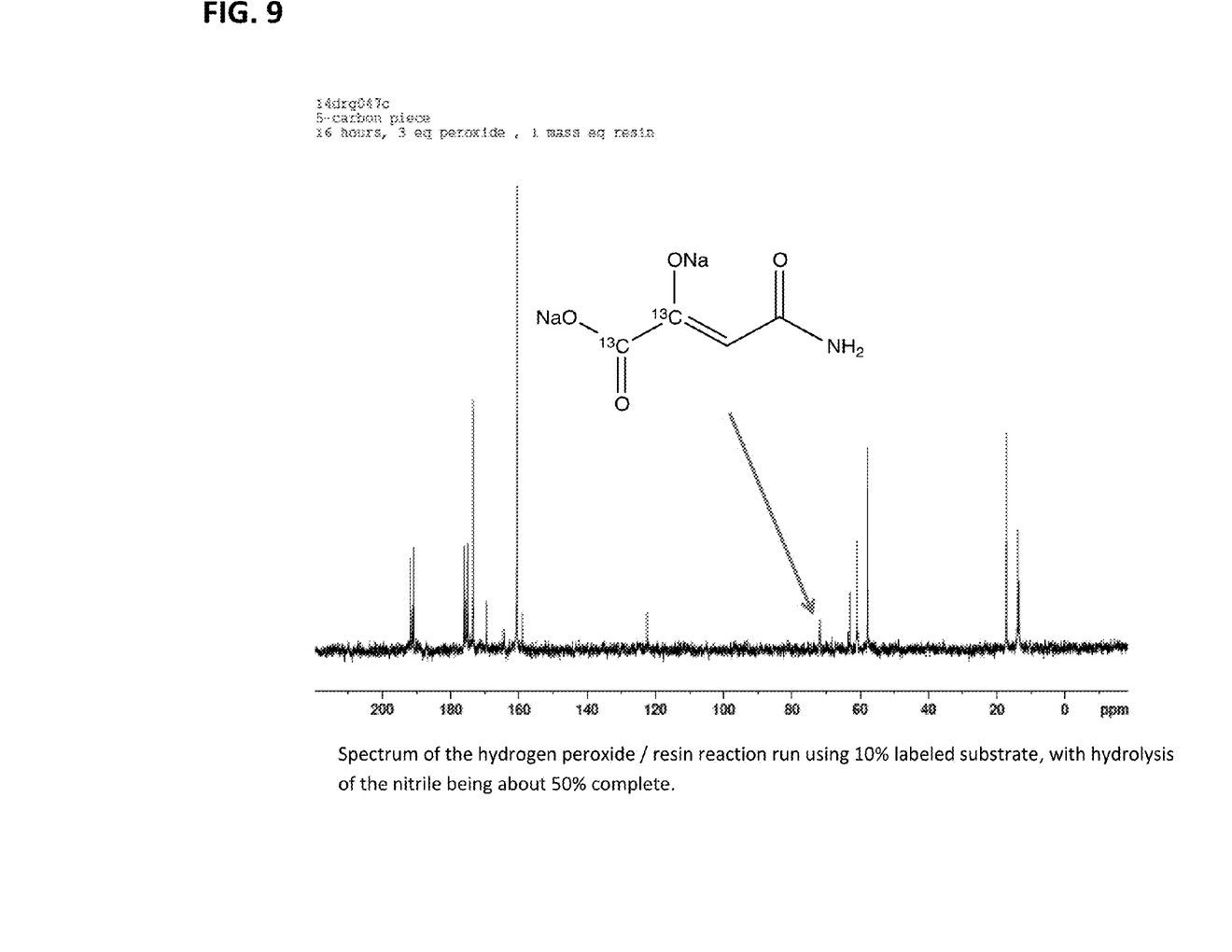
FIG. 9 is a spectrum of the hydrogen peroxide/resin reaction run using 10% labeled substrate.

Set forth in FIGS. 7-9 are spectra for comparison.

Note that the pH=10-11 in FIG. 8. The important peak for the illustrated carbon (shown with the arrow) is seen as the enolate, at ~73 ppm. The large peaks at 58 and 17 are ethanol from the hydrolyzed and decarboxylated ester.

FIG. 9 is the spectrum of the hydrogen peroxide/resin reaction run using 10% labeled substrate. The labels are at carbons 1 and 2 for the carboxylic acid and the ketone. FIG. 9 is taken at 16 hours at room temperature. The hydrolysis of the nitrile is about 50% complete.

Figure 5:
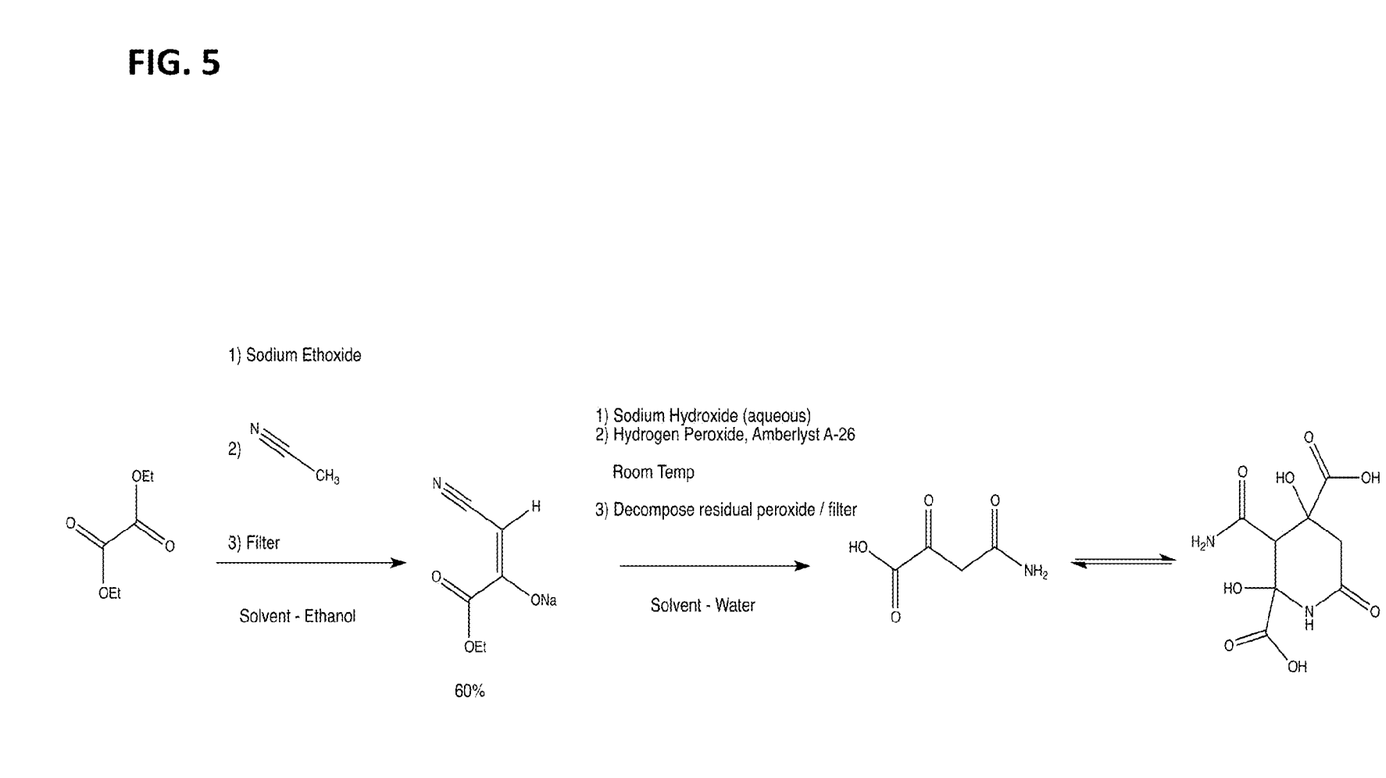
FIG. 5 is a diagram of another embodiment of an overall process of the present invention

It is to be appreciated that the alternate route shown in FIG. 5 to the desired compound makes the synthesis more economical. This route using acetonitrile in place of ethyl cyanoacetate is approximately 300% less expensive for starting materials per mole of product.

The 4-amino-2,4-dioxobutanoic acid may be used as a foliar spray on the leaves on agricultural crops. Plants would respond to treatments of such a spray by increasing their tillers. On cereal plants (for example, wheat, rice, barley), these are the structures on which the grain heads form and are developed. Thus, the greater number of tillers, the greater the number of seed heads, which translates into greater grain yield. Soybeans would respond to 4-amino-2,4-dioxobutanoic acid by increasing their root nodules, the site of biological reduction of $N_2$ gas from the atmosphere to ammonia which the plants can use as a nitrogen source. This means that less expensive nitrogen-containing fertilizer would be needed by the farmer.

Although the present invention has been described with reference to specific details, it is not intended that such details should be regarded as limitations upon the scope of the invention, except as and to the extent that they are included in the accompanying claims.

What is claimed is:

1. A process for synthesizing 4-amino-2,4-dioxobutanoate, comprising:
    reacting a dialkyl oxalate with an alkoxide in an alcoholic solvent to form a reaction mixture, and afterward
    adding an alkyl cyanoacetate to the reaction mixture and allowing a reaction to proceed under conditions suitable to form a first reaction product of the formula diethyl 2-cyano-3-hydroxy-butenedioate,
    isolating said first reaction product of diethyl 2-cyano-3-hydroxy-butenedioate,
    reacting said first reaction product of diethyl 2-cyano-3-hydroxy-butenedioate with aqueous hydroxide under conditions suitable to form 4-amino-2,4-dioxobutanoate.

2. The process of claim 1 further comprising acidifying said 4-amino-2,4-dioxobutanoate to form 4-amino-2,4-dioxobutanic acid.

3. The process of claim 1 wherein said dialkyl oxalate is diethyl oxalate.

4. The process of claim 1 wherein said alkyl cyanoacetate is ethyl cyanoacetate.

5. The process of claim 1 wherein said alkoxide is sodium ethoxide.

6. The process of claim 1 wherein said alcoholic solvent is ethanol.

7. The process of claim 1 wherein said alkoxide is selected from the group consisting of sodium ethoxide, potassium ethoxide, lithium ethoxide, cesium ethoxide and calcium ethoxide.

8. A process for synthesizing 4-amino-2,4-dioxobutanoate, comprising:
    reacting a dialkyl oxalate with an alkoxide in a first suitable solvent to form a reaction mixture, and afterward
    adding an alkyl cyanoacetate to the reaction mixture, and afterward
    extracting the reaction mixture with a suitable organic solvent and water to form an organic layer and an aqueous layer,
    then separating the aqueous layer from the organic layer,
    then acidifying the aqueous layer and extracting the acidified aqueous layer with additional suitable organic solvent to form a second aqueous layer and a second organic layer,
    then isolating diethyl-2-cyano-3-hydroxy-butenedioate from the second organic layer,
    then reacting the diethyl-2-cyano-3-hydroxy-butenedioate with an aqueous hydroxide under conditions suitable to form 4-amino-2,4-dioxobutanoate.

9. The process of claim 8 further comprising acidifying said 4-amino-2,4-dioxobutanoate to form 4-amino-2,4-dioxobutanic acid.

10. The process of claim 8, wherein the suitable organic solvent for extracting the reaction mixture is dichloromethane.

11. The process of claim 8 wherein the first and second organic layers are combined, and the diethyl-2-cyano-3-hydroxy-butenedioate is isolated from the combined organic layers.

12. The process of claim 8 wherein said alkoxide is selected from the group consisting of sodium ethoxide, potassium ethoxide, lithium ethoxide, cesium ethoxide and calcium ethoxide.

13. The process of claim 8 wherein said dialkyl oxalate is diethyl oxalate.

14. The process of claim 8 wherein said alkyl cyanoacetate is ethyl cyanoacetate.

15. The process of claim 8 wherein said alkoxide is sodium ethoxide.

16. The process of claim 8 wherein said first suitable solvent is ethanol.

17. The process of claim 8 wherein said alkoxide is selected from the group consisting of sodium ethoxide, potassium ethoxide, lithium ethoxide, cesium ethoxide and calcium ethoxide.

\* \* \* \* \*